US012751921B2

(12) United States Patent
Zhu et al.

(10) Patent No.: US 12,751,921 B2
(45) Date of Patent: Oct. 6, 2026

(54) MEDICATION THAT PROTECTS THE INTESTINAL MICROBIOTA AND THEIR PREPARATION METHODS AND APPLICATIONS

(71) Applicant: UNIVERSITY OF SCIENCE AND TECHNOLOGY OF CHINA, Anhui (CN)

(72) Inventors: Shu Zhu, Anhui (CN); Yucai Wang, Anhui (CN); Guorong Zhang, Anhui (CN); Qin Wang, Anhui (CN); Wanyin Tao, Anhui (CN); Wei Jiang, Anhui (CN)

(73) Assignee: UNIVERSITY OF SCIENCE AND TECHNOLOGY OF CHINA, Anhui (CN)

( * ) Notice: Subject to any disclaimer, the term of this patent is extended or adjusted under 35 U.S.C. 154(b) by 327 days.

(21) Appl. No.: 18/036,397

(22) PCT Filed: Nov. 13, 2020

(86) PCT No.: PCT/CN2020/128693
§ 371 (c)(1),
(2) Date: May 10, 2023

(87) PCT Pub. No.: WO2022/099617
PCT Pub. Date: May 19, 2022

(65) Prior Publication Data

US 2023/0330020 A1 Oct. 19, 2023

(51) Int. Cl.
*A61K 9/1272* (2025.01)
*A61K 9/1277* (2025.01)
(Continued)

(52) U.S. Cl.
CPC .......... *A61K 9/1272* (2013.01); *A61K 9/1277* (2013.01); *A61K 31/43* (2013.01);
(Continued)

(58) Field of Classification Search
CPC .................................................... A61K 9/1272
See application file for complete search history.

(56) References Cited

U.S. PATENT DOCUMENTS

2004/0266701 A1* 12/2004 Fenical .............. A61K 31/7048
514/28
2010/0266491 A1* 10/2010 Farokhzad .............. A61P 15/00
424/9.4

(Continued)

FOREIGN PATENT DOCUMENTS

CN 1691923 11/2005
CN 103622902 3/2014

(Continued)

OTHER PUBLICATIONS

Manoj Narah and Narendra K. Jain. "Preparation, Characterization and Evaluation of Targeting Potential of Amphotericin B-Loaded Engineered PLGA Nanoparticles." Pharmaceutical Research, vol. 26 No. 12, Dec. 2009, pp. 2588-2598. (Year: 2009).*

(Continued)

*Primary Examiner* — Isaac Shomer
(74) *Attorney, Agent, or Firm* — JCIPRNET

(57) ABSTRACT

An orally administered antibiotic encapsulated in nanospheres, as well as its preparation method and application. The antibiotic encapsulated in the nanospheres includes an antibiotic and a degradable biocompatible polymer that encapsulates the antibiotic, wherein biocompatible polymer includes monosaccharide-modified poly (ethylene glycol)-poly(lactic-co-glycolic acid) (PEG-PLGA), which can significantly improves the damage caused by oral antibiotics to
(Continued)

the intestinal microbiota, avoids destruction of the microbial community, thereby preventing chronic diseases associated with intestinal microbial imbalance, and a good biocompatibility and long-term safety.

10 Claims, 6 Drawing Sheets

Specification includes a Sequence Listing.

(51) Int. Cl.

| | |
|---|---|
| ***A61K 31/43*** | (2006.01) |
| ***A61K 31/7036*** | (2006.01) |
| ***A61K 38/14*** | (2006.01) |
| ***A61K 47/26*** | (2006.01) |
| ***A61K 47/34*** | (2017.01) |

(52) U.S. Cl.

CPC .......... *A61K 31/7036* (2013.01); *A61K 38/14* (2013.01); *A61K 47/26* (2013.01); *A61K 47/34* (2013.01)

(56) References Cited

U.S. PATENT DOCUMENTS

| | | | | |
|---|---|---|---|---|
| 2018/0085458 A1* | 3/2018 | Nyborg | ................ | A61K 39/395 |
| 2018/0339015 A1* | 11/2018 | Zale | ........................ | A61P 31/04 |
| 2022/0184147 A1* | 6/2022 | Blaustein | ............. | A61K 31/704 |

FOREIGN PATENT DOCUMENTS

| | | | | |
|---|---|---|---|---|
| CN | 107261110 | | 10/2017 | |
| CN | 110170057 A | * | 8/2019 | ............. A61K 47/62 |
| CN | 111789810 | | 10/2020 | |
| WO | 03024426 | | 3/2003 | |
| WO | 03024430 | | 3/2003 | |
| WO | WO-2019133916 A1 | * | 7/2019 | ........... A61K 31/546 |
| WO | WO-2019135715 A1 | * | 7/2019 | ............. A61K 38/14 |

OTHER PUBLICATIONS

Régis Coco et al. "Drug delivery to inflamed colon by nanoparticles: Comparison of different strategies." International Journal of Pharmaceutics, vol. 440, 2013, pp. 3-12. (Year: 2013).*

Bohong Guo, Yi Cheng, Niying Li, Xiaofang Li, Miaozhen Jin, Ting Li, and Jin Li. "In vitro and in vivo studies of galactose-modified liver-targeting liposomes." Journal of Drug Targeting, vol. 21(3), 2013, pp. 257-264. (Year: 2013).*

Bjørn S. Madsen, Troels Havelund, and Aleksander Krag. "Targeting the Gut-Liver Axis in Cirrhosis: Antibiotics and Non-Selective b-Blockers." Advanced Therapeutics, vol. 30, 2013, pp. 659-670. (Year: 2013).*

Mingxia Liu et al. "Importance of Polymer Length in Fructose-Based Polymeric Micelles for an Enhanced Biological Activity." Macromolecules, vol. 52, 2019, pp. 477-486. (Year: 2019).*

Renu Suthar and Naveen Sankhyan. "Bacterial Infections of the Central Nervous System." Indian Journal of Pediatrics, vol. 86(1), Jan. 2019, pp. 60-69. (Year: 2019).*

English Translation of CN 110170057 A. "A Nano-particle Preparation Method Of Tf Modified Load Medicine And Application Thereof." Downloaded by examiner on Dec. 31, 2025, originally published in Chinese on Aug. 27, 2019, pp. 1-9. (Year: 2019).*

Fulan Xie et al. "Investigation of glucose-modified liposomes using polyethylene glycols with different chain lengths as the linkers for brain targeting." International Journal of Nanomedicine, vol. 7, 2012, pp. 163-175. (Year: 2012).*

Norbert Pardi et al. "Expression kinetics of nucleoside-modified mRNA delivered in lipid nanoparticles to mice by various routes." Journal of Controlled Release, vol. 217 (2015), pp. 345-351. (Year: 2015).*

"International Search Report (Form PCT/ISA/210) of PCT/CN2020/128693", mailed on Jul. 28, 2021, with English translation thereof, pp. 1-8.

Usha Stiefel et al., "Oral Administration of b-Lactamase Preserves Colonization Resistance of Piperacillin-Treated Mice", Brief Report, vol. 188, Nov. 2003, pp. 1605-1609.

Jean De Gunzburg et al., "Targeted Adsorption of Molecules in the Colon With the Novel Adsorbent-Based Medicinal Product, DAV132: A Proof of Concept Study in Healthy Subjects", The Journal of Clinical Pharmacology, vol. 55, Issue 1, May 2014, pp. 10-16.

Lu Zhang et al., "Antibiotic Administration Routes Significantly Influence the Levels of Antibiotic Resistance in Gut Microbiota", Antimicrobial Agents and Chemotherapy, vol. 57, Issue 8, Aug. 2013, pp. 3659-3666.

"Written Opinion of the International Searching Authority (Form PCT/ISA/237) of PCT/CN2020/128693", mailed on Jul. 28, 2021, pp. 1-7.

* cited by examiner

MEDICATION THAT PROTECTS THE INTESTINAL MICROBIOTA AND THEIR PREPARATION METHODS AND APPLICATIONS

CROSS-REFERENCE TO RELATED APPLICATION

This application is a 371 of international application of PCT application serial no. PCT/CN2020/128693, filed on Nov. 13, 2020. The entirety of the above-mentioned patent application is hereby incorporated by reference herein and made a part of this specification.

REFERENCE TO A SEQUENCE LISTING

The instant application contains a Sequencing Listing which has been submitted electronically in ASCII format and is hereby incorporated by reference in its entirety. Said ASCII copy, filed on Jun. 29, 2023, is named 133633_SEQUENCELISTING and is 25,803 bytes in size.

TECHNICAL FIELD

The present invention belongs to the field of biomedical technology, and specifically relates to a pharmaceutical composition for protecting gut microbiota, its preparation method and application, wherein the pharmaceutical composition has the effect of maintaining gut microbiota stability while treating microbial infections, treating diabetes, inhibiting gastric acid secretion, and promoting defecation.

BACKGROUND ART

Oral antibiotics are the most commonly effective drugs for treating bacterial infections in multiple organs of the human body. However, during the treatment process, the part of the oral antibiotics that is not absorbed by the intestines will remain in the intestines, causing great disturbance to the human microbiota. The symbiotic microorganisms in the human body interact with many physiological processes and participate in the regulation of immune and metabolic homeostasis. Therefore, exposure to antibiotics in the intestines can change this homeostasis, promote acute infections and chronic diseases such as the invasion of pathogenic microorganisms and obesity. In addition, excessive use of antibiotics can promote the development of bacterial resistance, making it increasingly difficult to control bacterial infections.

Scientists have developed strategies to protect gut microbiota from the harmful consequences of ecological disruption during antibiotic therapy. For example, in 2003, Usha Stiefei suggested that oral administration of beta-lactamase can prevent the impact of residual beta-lactam antibiotics on gut microbiota and maintain the gut in a colonized and resistant state. However, this approach is limited to beta-lactam antibiotics only. In 2014, Jean de Gunzburg studied the delivery of non-specific adsorbents such as activated charcoal to the ileum or colon to reduce fecal concentration of orally administered antibiotics such as ciprofloxacin or amoxicillin, without affecting plasma pharmacokinetics, but this method increased the number of administrations. In 2013, Wanghua et al. proposed other administration routes, such as intravenous injection of antibiotics, which can reduce the level of antibiotic residue in the gut and prevent the rise of gut microbial resistance. Although this is beneficial to the gut microbiota, it is inconvenient for home use. Therefore, there is an urgent need to develop more convenient alternative methods to address the imbalance of gut microbiota caused by oral antibiotics.

SUMMARY OF THE INVENTION

The invention relates to a pharmaceutical composition for protecting gut microbiota, its preparation method and application, with the aim of increasing the absorption of a pharmaceutical composition in the proximal small intestine, prolonging the circulation of pharmaceutically active ingredient, and reducing the residual amount of pharmaceutically active ingredient in the intestine where there is a rich bacterial population, thus protecting the ecological balance of intestinal microbiota.

To achieve the above objectives, on the one hand, the invention proposes a medication, including the pharmaceutically active ingredient and a biodegradable and biocompatible polymer that encapsulated the pharmaceutically active ingredient. The biocompatible polymer includes monosaccharide-modified poly (ethylene glycol)-poly (lactic-co-glycolic acid) (PEG-b-PLGA).

In some embodiments, the pharmaceutically active ingredient is an active pharmaceutical ingredient that affects the intestinal microbiota or an active pharmaceutical ingredient that mimics changing the absorption site to the small intestine.

In some embodiments, the pharmaceutically active ingredient that affect the intestinal microbiota include one or more of proton pump inhibitors, metformin, antibiotics, and laxatives.

In some embodiments, the monosaccharide-modified poly (ethylene glycol)-poly(lactic-co-glycolic acid) is selected from one or more of glucose-PEG-PLGA, fructose-PEG-PLGA, fucose-PEG-PLGA, galactose-PEG-PLGA, and mannose-PEG-PLGA.

In some embodiments, the weight ratio of the pharmaceutically active ingredients to the biodegradable biocompatible polymer is 1:0.5-5 (e.g., 1:1, 1:2, 1:3, or 1:4).

In some embodiments, the pharmaceutically active ingredients further comprise cationic lipids.

In some embodiments, the cationic lipids are selected from one or more of 1,2-dioleoyl-3-trimethylammonium-propane chloride (DOTAP), 2,3-dioleyloxy-N-[2(sperminecarboxamido)ethyl]-N,N-dimethyl-1-propanaminium trifluoroacetate (DOTMA), and cholesterol analogs bearing a cationic headgroup, such as 3β-[N—(N',N'-dimethylaminoethane)carbamoyl] cholesterol (DC-Chol).

In some embodiments, the weight ratio of the pharmaceutically active ingredients to the cationic lipid is 1:0.1-1 (for example, 1:0.2, 1:0.3, 1:0.5, or 1:0.8).

In some embodiments, the antibiotic is selected from one or more of the quinolone antibiotics, β-lactam antibiotics, macrolide antibiotics, aminoglycoside antibiotics, oxazolidinone antibiotics, nitroimidazole antibiotics, tetracycline antibiotics, and glycopeptide antibiotics. For example, the antibiotic may be selected from antibacterial agents such as clarithromycin, amoxicillin, metronidazole, tetracycline, neomycin, and vancomycin.

On the other hand, the present invention also proposes a method for preparing medication. The method involves using biocompatible and degradable polymers to encapsulate the pharmaceutically active ingredients through double emulsion, single emulsion, dialysis, nanoprecipitation, thin film hydration, or microfluidic mixing, preferably with the addition of cationic lipids during the preparation process.

In some embodiments, hydrophilic pharmaceutically active ingredients are encapsulated using double emulsion or thin film hydration, while hydrophobic pharmaceutically active ingredients are encapsulated using dialysis, nanoprecipitation, microfluidic mixing, or single emulsion.

For example, the steps for wrapping hydrophilic pharmaceutically active ingredients using the double emulsion method may include:

(1) Adding the pharmaceutically active ingredients solution and degradable biocompatible polymer into a volatile organic solvent and ultrasonically emulsifying to obtain an oil-in-water emulsion.

(2) Adding the oil-in-water emulsion into a large amount of water and ultrasonically emulsifying again to obtain a water-in-oil-in-water emulsion.

(3) Evaporating the volatile organic solvent, washing away free pharmaceutically active ingredients, and obtaining the nanoparticle-wrapped oral pharmaceutically active ingredients.

The volatile organic solvent is selected from one or more of dichloromethane, trichloromethane, and ethyl acetate, and the emulsification time is 0.5-2 minutes.

The steps for encapsulating hydrophobic pharmaceutically active ingredients using dialysis may include:

Dissolving the pharmaceutically active ingredients and biodegradable biocompatible polymer in an organic solvent, adding water and stirring to obtain nanoparticles loaded with the pharmaceutically active ingredients, dialyzing and removing free pharmaceutically active ingredients to obtain orally administered pharmaceutically active ingredients encapsulated by nanoparticles.

The steps for encapsulating hydrophobic pharmaceutically active ingredients using a single emulsion method may include:

(1) adding an aqueous solution of the pharmaceutically active ingredients and biodegradable biocompatible polymer to a volatile organic solvent, and ultrasonically emulsifying to obtain a water-in-oil emulsion.

(2) evaporating the volatile organic solvent, washing to remove free pharmaceutically active ingredients, and obtaining orally administered pharmaceutically active ingredients encapsulated by nanoparticles.

The volatile organic solvent can be one or more of dichloromethane, chloroform, and ethyl acetate, and the emulsification time is 0.5-2 minutes.

On the other hand, the present invention also proposes a use of the medication in the preparation of drugs for treating bacterial infectious diseases, treating diabetes, inhibiting gastric acid secretion, and promoting defecation. For example, bacterial infectious diseases may include pneumococcal infections or other microbial infections.

Compared with the prior art, the advantages of the medication proposed by the present invention are as follows:

1. The use of glucose-modified cationic nanoparticles (PGNPs) to enclose pharmaceutically active ingredients in the present invention allows for rapid absorption in the proximal small intestine after oral administration, with minimal intestinal residue.

2. The use of PGNPs to enclose pharmaceutically active ingredients in the present invention enables rapid absorption into the bloodstream after oral administration.

3. The medication antibiotics enclosed in nanoparticles in the present invention do not alter the therapeutic effect of pharmaceutically active ingredients and allow for the treatment of hydrophobic and hydrophilic pharmaceutically active ingredients using PGNPs, thereby reducing disease symptoms.

4. The medication enclosed in nanoparticles in the present invention can significantly reduce the damage of pharmaceutically active ingredients to the intestinal flora.

5. The medication enclosed in nanoparticles in the present invention can avoid destruction of the microbial community, thus preventing chronic diseases associated with ecological imbalance.

6. The medication enclosed in nanoparticles in the present invention have biocompatibility and long-term safety.

BRIEF DESCRIPTION OF THE DRAWINGS

To provide a clearer illustration of the technical solutions in the present application or existing technology, a brief introduction to the required figures in the embodiments will be given below.

NPs refer to nanoparticles; GNPs refer to glucose-modified nanoparticles; PNPs refer to cationic nanoparticles; PGNPs refer to glucose-modified cationic nanoparticles.

Figure 2:
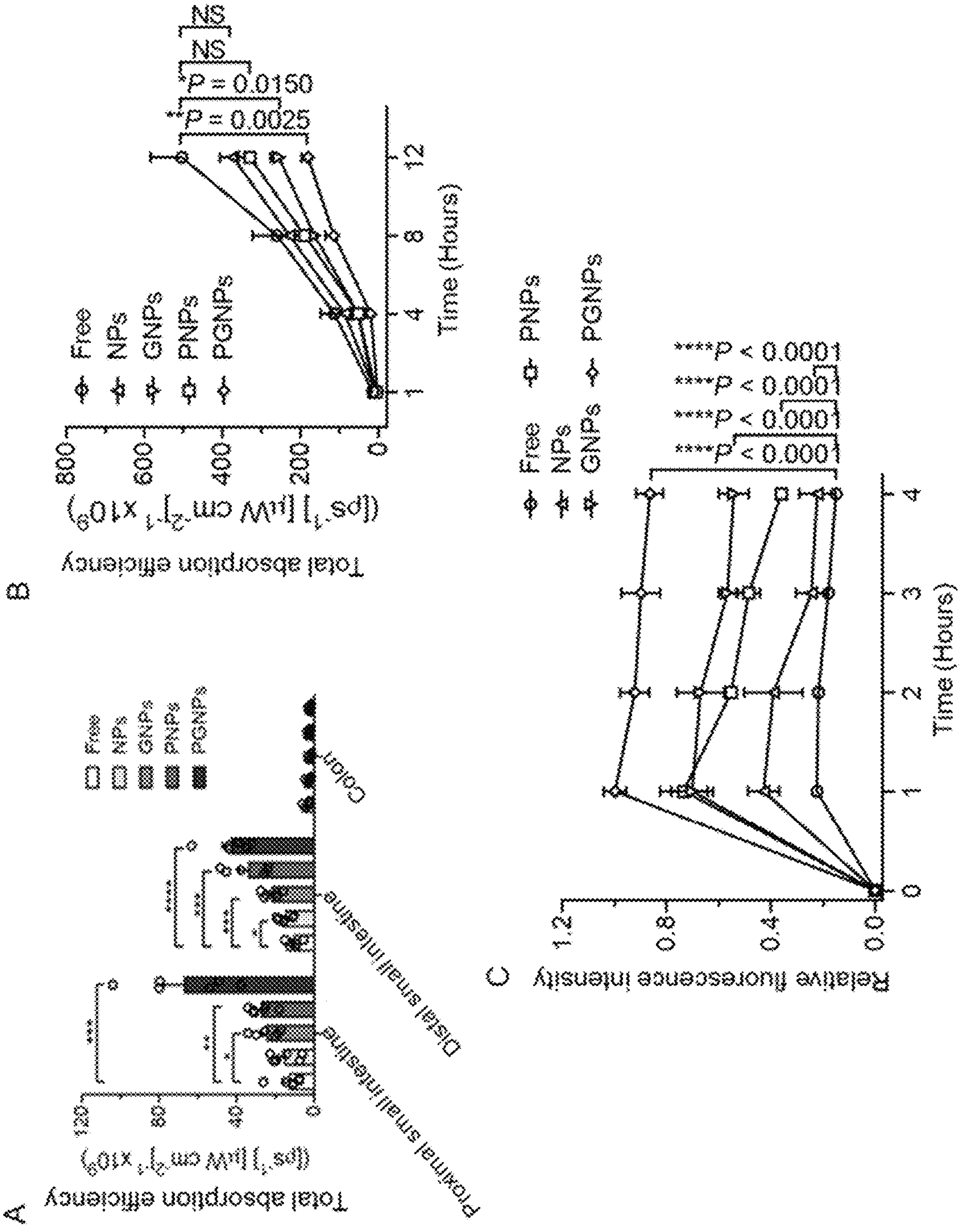

FIG. 2: The fluorescent dye DiD, which stands for 1,1'-Dioctadecyl-3,3,3',3'-Tetramethylindodicarbocyanine, 4-Chlorobenzenesulfonate Sal, was used to label different nanoparticles. The absorption and fecal residue of the nanoparticles in the intestine, as well as their distribution in the blood, were analyzed by measuring fluorescence intensity at different time points after orally administering them to mice. Panel A shows the absorption of different fluorescently labeled nanoparticles in different segments of the intestine one hour after oral administration. Panel B shows the fecal residue of different fluorescently labeled nanoparticles in the intestine after oral administration. Panel C shows the fluorescence intensity analysis of the nanoparticles in the blood after oral administration. *: $P<0.05$; : $P<0.01$; *: $P<0.001$; ****: $P<0.0001$.

Free refers to free fluorescent dye DiD; NPs refers to nanoparticles; GNPs refers to glucose-modified nanoparticles; PNPs refers to cationic nanoparticles; PGNPs refers to glucose-modified cationic nanoparticles. n.s. indicates no significant difference.

Figure 3:
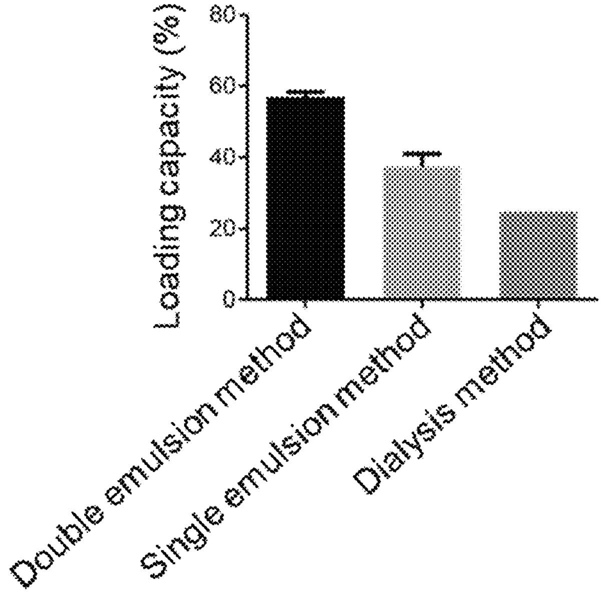

FIG. 3: PGNPs were obtained by screening and used to encapsulate antibiotics. The loading rates of hydrophilic and hydrophobic antibiotics were determined by double-emulsion, single-emulsion, and dialysis methods. The results indicated that the double-emulsion method can effectively encapsulate hydrophilic antibiotics.

Figure 4:
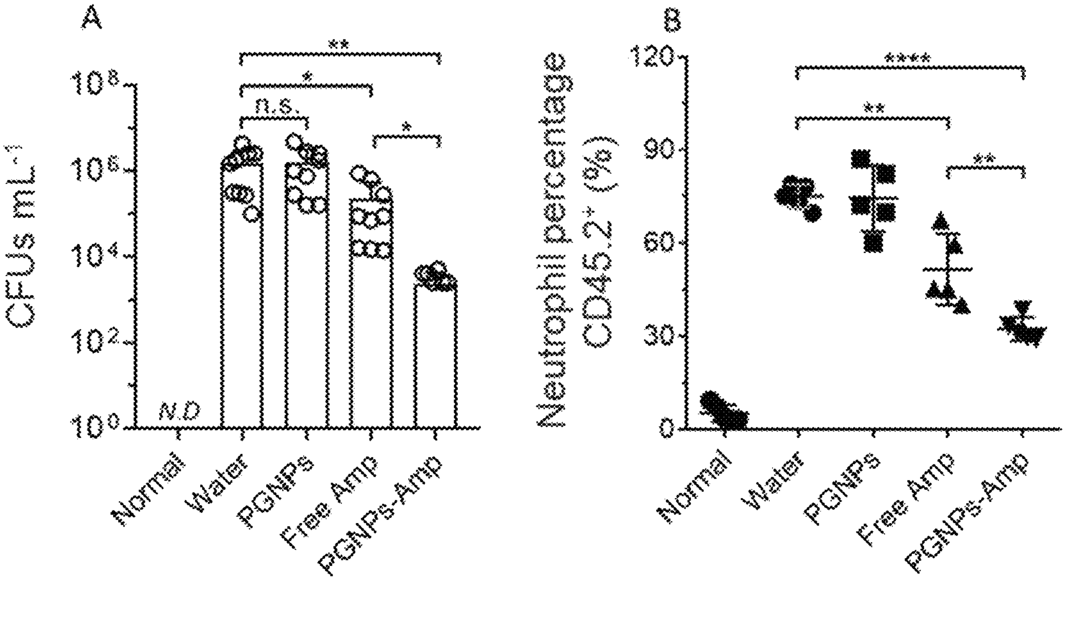

FIG. 4: Treatment of *Streptococcus pneumoniae*-induced pneumonia with PGNPs-encapsulated ampicillin. Panel A compares the number of *S. pneumoniae* in the lungs of mice treated with free ampicillin (Free-Amp) and PGNPs-encapsulated ampicillin (PGNPs-Amp), as well as mice not treated with ampicillin (Water, PGNPs). Panel B compares the percentage of neutrophil infiltration in the lungs of each group. *: $P<0.05$; : $P<0.01$; *: $P<0.001$; ****: $P<0.0001$.

Normal, healthy control; Water, control group given water orally; PGNPs, control group given empty particles orally; Free Amp, experimental group given free ampicillin orally; PGNPs-Amp, experimental group given glucose-modified cationic nanoparticles encapsulated ampicillin orally. N.D., not detected. n.s., not significant.

Figure 5:
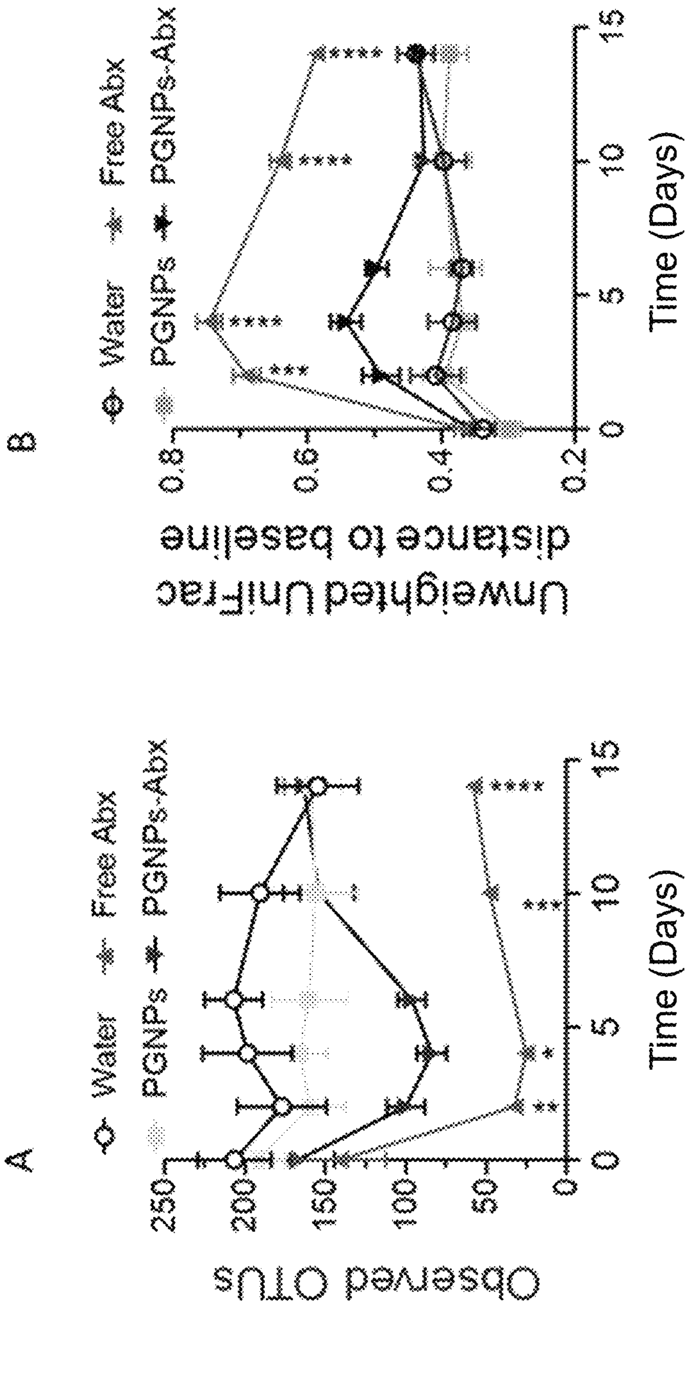

FIG. 5: Comparison of the destruction of gut microbiota among control group, orally administered free antibiotics (Free-Abx) and antibiotics encapsulated in PGNPs (PGNPs-Abx). Panel A shows the comparison of α-diversity among different groups, while panel B compares β-diversity between the control group and the two antibiotic treatment groups. *: P<0.05; : P<0.01; *: P<0.001; ****: P<0.0001.

Water: control group orally administered water; PGNPs: control group orally administered empty particles; Free-Abx: experimental group orally administered free antibiotics; PGNPs-Abx: experimental group orally administered glucose-modified cationic nanoparticle-encapsulated antibiotics.

Figure 6:
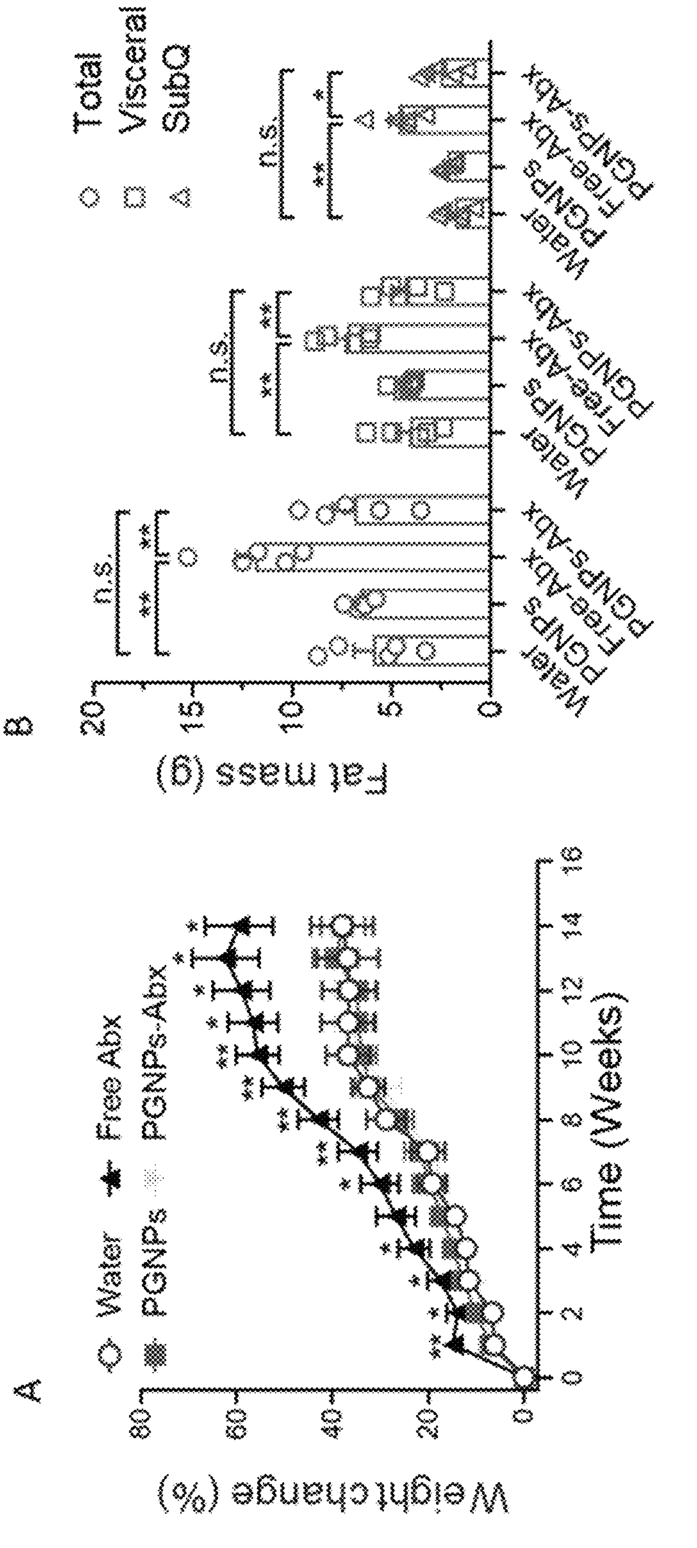

FIG. 6: Comparison of the effects of oral free antibiotics (Free-Abx) and antibiotics encapsulated in PGNPs (PGNPs-Abx) on metabolic disease obesity. A graph shows the body weight of mice in the antibiotic-treated and control groups. B graph shows the weight of adipose tissue in each group. *: P<0.05; : P<0.01; *: P<0.001; ****: P<0.0001.

Water, control group receiving oral water; PGNPs, control group receiving oral empty particles; Free Abx, experimental group receiving oral free antibiotics; PGNPs-Abx, experimental group receiving antibiotics encapsulated in glucose-modified cationic nanoparticles. n.s., no significant difference.

Figure 7:
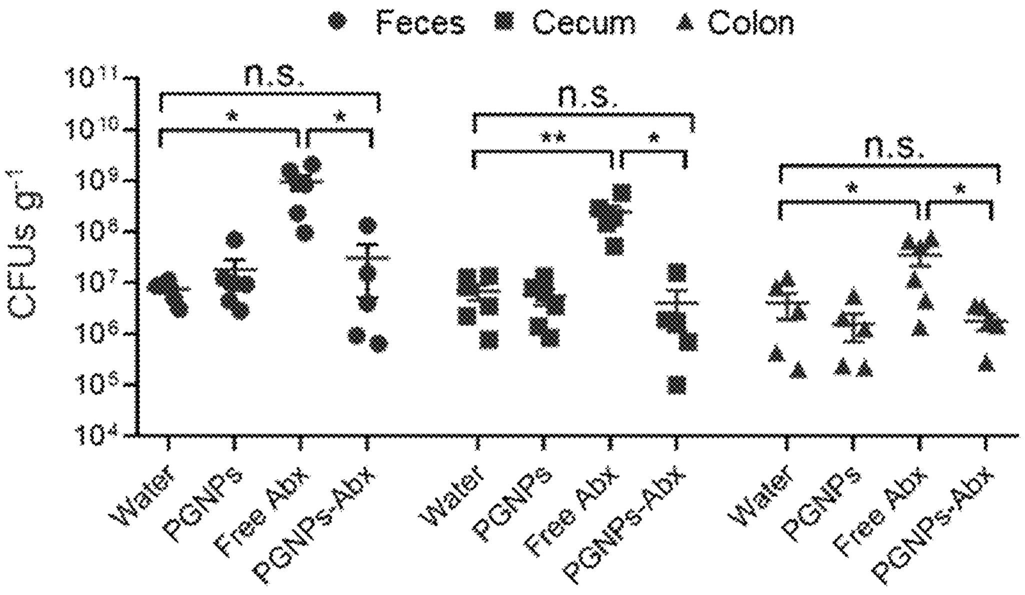

FIG. 7: Effects of comparing the control group with orally administered free antibiotics (Free-Abx) and antibiotics encapsulated in PGNPs (PGNPs-Abx) on the ability of mice to resist *Citrobacter rodentium* infection. The graph shows the bacterial counts in feces, cecum, and colon. *: P<0.05; : P<0.01; *: P<0.001; ****: P<0.0001.

Water, control group receiving orally administered water; PGNPs, control group receiving orally administered empty particles; Free Abx, experimental group receiving orally administered free antibiotics; PGNPs-Abx, experimental group receiving orally administered glucose-modified cationic nanoparticle-encapsulated antibiotics. n.s., no significant difference.

Figure 8:
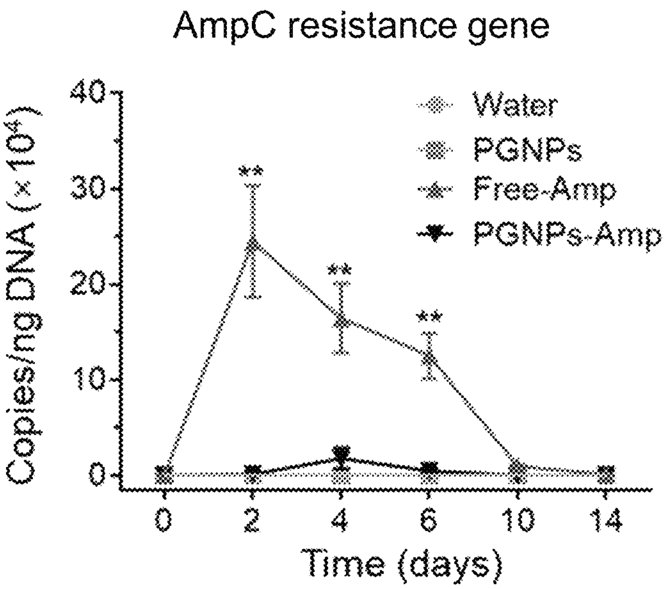

FIG. 8: Comparison of the impact of oral administration of Free-Abx (free antibiotics) and antibiotics encapsulated in PGNPs (PGNPs-Abx) on the intestinal resistance gene β-lactamase ampC in the control group. *: P<0.05; : P<0.01; *: P<0.001; ****: P<0.0001.

Water, oral administration of water in the control group; PGNPs, oral administration of empty particles in the control group; Free Abx, oral administration of free antibiotics in the experimental group; PGNPs-Abx, oral administration of glucose-modified cationic nanoparticle-encapsulated antibiotics in the experimental group.

DETAILED DESCRIPTION OF THE EMBODIMENTS

To clarify and facilitate understanding of the purpose, technical solution, and advantages of the present invention, specific embodiments are described below and detailed explanations are provided with reference to the accompanying drawings.

In the description of the present invention, the term "an embodiment" refers to at least one embodiment in which specific features, structures, parameters, steps, or the like are described. Therefore, in the description of the present invention, if phrases such as "in one embodiment according to the present invention" or "in an embodiment" are used, they are not intended to specifically refer to the same embodiment. Similarly, if phrases such as "in another embodiment", "in a different embodiment according to the present invention", or "in another embodiment according to the present invention" are used, they are not intended to indicate that the mentioned features can only be included in specific, different embodiments. Those skilled in the art should understand that specific features, structures, parameters, steps, and the like disclosed in one or more embodiments in the present invention specification can be combined in any suitable manner.

To address the deficiencies of existing application methods, this application provides a type of nanoparticle used to encapsulate antibiotics. After oral administration, the nanoparticle can be quickly absorbed into the bloodstream in the small intestine, thereby exerting its antibacterial effect while avoiding damage to the gut microbiome caused by residual antibiotics in the intestinal tract. Based on the technical scheme of the present invention, different types of nanoparticles labeled with fluorescent dye DiD were designed and synthesized for screening the most absorbable nanoparticle in the intestinal tract for subsequent antibiotic encapsulation. Antibiotics encapsulated by these nanoparticles can facilitate absorption in the proximal small intestine. The nanoparticles are prepared using biodegradable and biocompatible polymers, including monosaccharide-modified poly(ethylene glycol)-poly(lactic-co-glycolic acid) (monosaccharide-modified PEG-PLGA).

In one embodiment, different types of nanoparticles (PGNPs, PNPs, GNPs, NPs) labeled with DiD dye were prepared using a double emulsion-solvent evaporation method. It was discovered that incorporating a certain proportion of cationic lipids, such as 1,2-dioleoyl-3-trimethylammonium-propane chloride (DOTAP), during the preparation of nanoparticles could render them positively charged. Since the membrane of intestinal epithelial cells is negatively charged, the interaction between the positive and negative charges can reduce the distance between the nanoparticles and the intestinal epithelial cells. Simultaneously, modifying the nanoparticles with glucose while adding cationic lipids can promote the interaction between the nanoparticles and the SGLT1 glucose transporter protein at the proximal small intestine, accelerating the entry of nanoparticles into the bloodstream.

Figure 1:
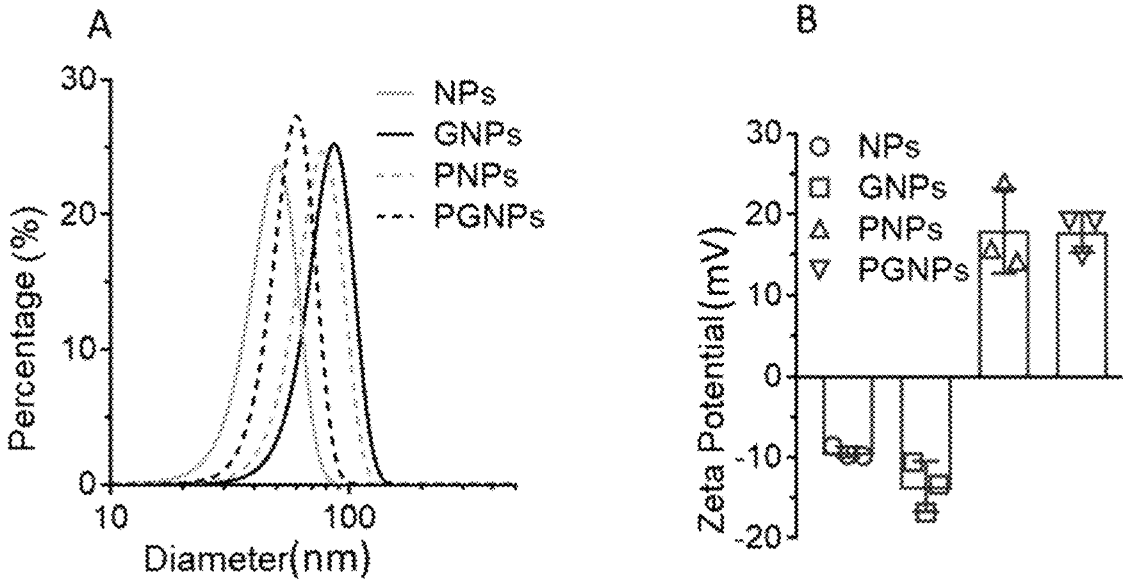
FIG. 1: Preparation of different types of nanoparticles (PGNPs, PNPs, GNPs, NPs) with a comparison of their size (A) and charge (B). It can be observed that the particle size is mainly concentrated around 80-100 nanometers, with some particles carrying positive charges and some carrying negative charges.

In this embodiment, DiD dye was added to 0.5 mL of dichloromethane containing 0.5 mg DOTAP and 5 mg glucose-PEG-PLGA (glucose-polyethylene glycol-poly(lactic-co-glycolic acid) copolymer) (Avanti Polar Lipids), and sonicated with a Vibra-Cell™ ultrasonic probe (Sonics & Materials, Newtown, CT, USA) at 80 W for 1 minute in an ice bath to form an oil-in-water emulsion. The resulting oil-in-water-in-water emulsion was then sonicated in 5 mL of Milli-Q water (80 W, 1 minute) to form water-in-oil-in-water emulsion while in an ice bath. Dichloromethane was removed by rotary evaporation. The resulting PGNPs-DiD were filtered three times through a 100,000 Da molecular weight cutoff ultrafiltration membrane (Millipore) to remove free dye. The process of preparing DiD-labeled PNPs was comparable to that of DiD-labeled PGNPs, except that PEG-PLGA was used instead of glucose-PEG-PLGA. The preparation of DiD-labeled GNPs was comparable to that of DiD-labeled PGNPs, except that 0.5 mg DOTAP was not added to the dichloromethane solution. The preparation of DiD-labeled NPs was comparable to that of DiD-labeled PGNPs, except that 0.5 mg DOTAP was not added to the dichloromethane solution and PEG-PLGA was used instead of glucose-PEG-PLGA. Panels A and B in FIG. 1 show the size and charge of different nanoparticles, respectively.

In one embodiment, different types of nanoparticles were screened and those that were well absorbed in the small intestine with minimal intestinal residue were selected for use in encapsulating antibiotics. Using fluorescently labeled nanoparticles of different types and administering them to mice orally, the fluorescence values in the intestinal cells and feces were measured at different time points using a small animal imaging system to determine the fluorescence absorption values and fecal residue values of the different nanoparticles in the intestine. In addition, confocal microscopy was used to observe the distribution of different nanoparticles in mouse blood vessels. The results are shown in FIG. 2. It was found that PGNPs-DiD were most absorbed in the small intestine with the least amount of intestinal residue. Furthermore, the fluorescence value in the blood was the highest and lasted for a longer time. Therefore, PGNPs were subsequently used to encapsulate antibiotics to study their effects on disease improvement and the impact on the gut microbiome, as well as the effects of microbiome disruption on related diseases.

In one implementation, we used a double-emulsification method to encapsulate hydrophilic antibiotics such as ampicillin and erythromycin, and measured an encapsulation efficiency of 50%-60%. Using a dialysis method, we encapsulated hydrophobic antibiotics such as metronidazole and achieved an encapsulation efficiency of 25%. Encapsulation of hydrophobic antibiotics such as metronidazole using a single-emulsification method yielded an encapsulation efficiency of 20%-40%. Various types of antibiotics with different properties can be encapsulated in nanoparticles using methods such as single-emulsification, double-emulsification, and dialysis, as shown in FIG. 3. The double-emulsification method yielded the highest encapsulation efficiency for hydrophilic antibiotics.

In one embodiment, antibiotics are encapsulated using screened PGNPs. A 30 μL water solution (100 mg $mL^{-1}$) of ampicillin or vancomycin was added to 0.5 mL of dichloromethane containing 0.5 mg DOTAP and 5 mg glucose-PEG-PLGA, and sonicated using a Vibra-Cell™ ultrasonic processor (Sonics & Materials, Newtown, CT, USA) at 80 W for 1 minute in an ice bath to form an oil-in-water emulsion. The resulting emulsion was then sonicated in 5 mL of Milli-Q water (80 W, 1 minute) to form a water-in-oil-in-water emulsion. Dichloromethane was then removed using a rotary evaporator. The resulting PGNPs-Amp and PGNPs-Van were obtained by three rounds of ultrafiltration using a molecular weight cutoff filter of 100,000 Da (Millipore) to remove free antibiotics.

In one implementation, the effectiveness of orally administered ampicillin wrapped in PGNPs for treating mouse pneumonia was validated. Firstly, we induced mouse pneumonia by intranasally administering *Streptococcus pneumoniae*. At 2 and 8 hours post-induction, the mice received either ampicillin encapsulated in PGNPs or free ampicillin treatment. At 24 hours post-infection, the number of *Streptococcus pneumoniae* in the mouse lungs and the proportion of neutrophil infiltration were analyzed. As shown in FIG. 4, ampicillin encapsulated in PGNPs and free ampicillin showed good therapeutic effects, with even better results observed for ampicillin encapsulated in PGNPs.

In one example, the effects of orally administered PGNPs-encapsulated ampicillin and vancomycin on the gut microbiota of mice were evaluated. Two forms of antibiotics, PGNPs-encapsulated and free, were orally administered to the mice once a day for five consecutive days. A control group was not treated with antibiotics. During and after the antibiotic treatment, fecal samples from the mice were collected and stored at −80° C. until subsequent 16S rRNA sequencing analysis. As shown in FIG. 5, sequencing analysis revealed no significant changes in the composition of the gut microbiota in mice treated with PGNPs-encapsulated antibiotics compared to the control group. However, significant changes in the composition and abundance of the gut microbiota were observed in mice treated with free antibiotics, indicating that PGNPs-encapsulated antibiotics have a protective effect on the gut microbiota of mice.

One example verified that orally administered antibiotics, which were encapsulated in PGNPs, did not cause obesity in mice. We orally administered ampicillin and vancomycin, both encapsulated in PGNPs, as well as free ampicillin and vancomycin to 5-week-old mice, with a control group receiving no antibiotic treatment. The mice were administered antibiotics once a day for 5 consecutive days. At 9 weeks of age, the mice were fed a high-fat diet, and their body weights were measured at specific time points, followed by analysis of their fat weights. As shown in FIG. 6, the analysis revealed that mice in the group receiving antibiotics encapsulated in PGNPs and the control group exhibited consistent trends in body weight and fat weight. In contrast, mice in the group receiving free antibiotics orally had relatively higher body weight and fat weight, indicating that antibiotics encapsulated in PGNPs could protect the intestinal microbiota from damage and prevent the occurrence of metabolic diseases and obesity caused by microbial dysbiosis.

In one embodiment, it was demonstrated that orally administered antibiotics encapsulated in PGNPs did not increase susceptibility of mice to opportunistic pathogens. We administered orally ampicillin and vancomycin, both encapsulated in PGNPs or in free form, to 6-8 weeks old mice, while the control group was not treated with antibiotics. Mice received daily oral gavage for consecutive days. On the second day after completion of the oral treatment, mice were orally infected with *Citrobacter rodentium*. On the 8th day post-infection, fecal, cecal, and colonic *Citrobacter rodentium* counts were analyzed. As shown in FIG. 7, mice treated with PGNPs-encapsulated antibiotics and control group showed a similar trend in *Citrobacter rodentium* counts. Conversely, mice treated with free antibiotics showed relatively higher bacterial counts, indicating that PGNPs-encapsulated antibiotics can protect the gut microbiota and resist opportunistic pathogen infections.

In one embodiment, it was demonstrated that oral administration of PGNPs-encapsulated ampicillin in mice did not increase the copy number of antibiotic resistance genes in gut bacteria. We orally administered PGNPs-encapsulated ampicillin and free ampicillin to 6-8 weeks old mice for 5 consecutive days, once a day, while the control group was not given any ampicillin treatment. At specific time points during and after the antibiotic treatment period, we collected fecal samples from the mice, extracted DNA, determined DNA concentration, diluted to 10 ng $\mu L^{-1}$, and analyzed the copy number of the ampicillin resistance gene ampC using real-time fluorescence quantitative PCR. As shown in FIG. 8, there was no significant change in the copy number of the gut bacterial resistance gene ampC in the mice treated with PGNPs-encapsulated ampicillin compared to the control group, while the copy number of ampC in the gut bacterial population of mice treated with free ampicillin increased sharply over time. This suggests that PGNPs-encapsulated ampicillin has a protective effect on the gut bacterial population in mice and does not lead to the accumulation of resistance genes.

The following specific example further illustrates the application of the present invention.

Example 1: Determination of the Loading Rates of Different Antibiotics Using Double Emulsion, Single Emulsion, and Dialysis Methods For hydrophilic antibiotics, such as ampicillin and vancomycin, the double emulsion method was used for loading. A water-soluble solution (100 mg $mL^{-1}$, 30 μL) of either ampicillin or vancomycin was added to 0.5 mL of dichloromethane containing 0.5 mg DOTAP and 5 mg glucose-PEG-PLGA. The mixture was sonicated for 1 minute at 80 W using a Vibra-Cell™ ultrasonic processor (Sonics & Materials, Newtown, CT, USA) on ice. The resulting oil-in-water emulsion was sonicated for an additional 1 minute at 80 W in 5 mL of Mili-Q water to form a water-in-oil-in-water emulsion on ice. The dichloromethane was then removed using a rotary evaporator. The resulting nanoparticles containing loaded antibiotics were purified using a centrifugal filter (molecular weight cutoff=100,000 Da, Millipore) three times to remove any unbound antibiotics. The purified nanoparticles were then centrifuged at 15,000 g for 2 hours to remove the supernatant, and the pellet was resuspended to obtain pure nanoparticles containing loaded antibiotics. The concentration of the loaded antibiotics in the nanoparticles was measured using a UV spectrophotometer or HPLC. The loading rate was calculated by dividing the mass of loaded antibiotics by the total mass of antibiotics used for loading. The loading rates for hydrophilic antibiotics were between 50% and 60%.

For hydrophobic antibiotics such as metronidazole, dialysis is used by dissolving the antibiotics in an organic solvent (such as DMSO). A clean magnetic stir bar is placed in a clean round-bottom flask, and 1 mL of Gluc-PEG-PLGA (10 mg $mL^{-1}$) polymer material dissolved in an organic solvent (such as DMSO) and 100 ul of cationic lipid (10 mg $mL^{-1}$) are added, followed by 100 ul of antibiotic (at a concentration based on its maximum solubility). The round-bottom flask is placed on a magnetic stirrer and stirred slowly, then the speed is increased and 5 mL of Milli-Q water is added, followed by stirring for an additional 2 minutes. The resulting mixture is filtered three times using an ultrafiltration tube (molecular weight cutoff=100,000 Da, Millipore) to remove free antibiotics and other impurities. The retained nanoparticles carrying antibiotics are placed in a 1.5 mL EP tube, centrifuged at 3000 rpm for 5 minutes, and the supernatant is taken to further remove free antibiotics. The concentration of nanoparticle-encapsulated antibiotics is measured using a UV spectrophotometer or HPLC, and the encapsulation efficiency is calculated by dividing the mass of encapsulated antibiotics by the total mass of antibiotics used, which is between 20% to 25%.

For hydrophobic antibiotics such as metronidazole, a single emulsion method can be used to encapsulate the antibiotic by dissolving it in a volatile organic solvent (such as ethyl acetate). 100 μL of the solution is added to 1 mL of dichloromethane containing 1 mg of DOTAP and 10 mg of glucose-PEG-PLGA. The mixture is sonicated at 80 W for 1 minute on ice using a Vibra-Cell™ ultrasonic cell disrupter (Sonics & Materials, Newtown, CT, USA). The dichloromethane is then removed using a rotary evaporator. The resulting nanoparticles containing the encapsulated antibiotic are filtered three times using a 100,000 Da molecular weight cutoff ultrafiltration membrane (Millipore) to remove free antibiotic and other impurities. The purified nanoparticles containing the encapsulated antibiotic are obtained by centrifugation at 3000 rpm for 5 minutes and collecting the supernatant. The concentration of the encapsulated antibiotic in the nanoparticles is measured using a UV spectrophotometer or HPLC. The encapsulation efficiency is calculated as the mass of encapsulated antibiotic divided by the total mass of input antibiotic. For hydrophilic antibiotics, the encapsulation efficiency is typically between 20% and 40%.

Example 2: Oral Administration of Antibiotic-Loaded PGNPs Effectively Treats Mouse Pneumonia Caused by *Streptococcus pneumoniae*

Experimental Methods

Mice were divided into four groups, with two control groups receiving no ampicillin treatment and two treatment groups receiving ampicillin treatment after infection, with at least 3 mice per group. Mouse pneumonia was induced by intranasal inoculation of $3\times10^{8}$ CFUs of *Streptococcus pneumoniae*. After infection, mice were orally treated with either free ampicillin or PGNPs encapsulated with ampicillin (40 mg $kg^{-1}$) at 2 hours and 8 hours post-infection. After 24 hours of infection, the number of *Streptococcus pneumoniae* in the lungs was measured. Mouse lung tissues were collected and homogenized in sterile PBS, diluted 10-fold in PBS, and plated for colony counting. The proportion of neutrophil infiltration in the lungs of the mice was determined by staining the lung tissues with antibodies and analyzing with a flow cytometer.

Experimental Results

The experimental results are shown in FIG. 4 regarding the effect of ampicillin treatment on mouse pneumonia. As indicated by the bacterial count and the proportion of neutrophils, it can be observed that the group of mice treated with ampicillin showed a significant decrease in the number of lung *Streptococcus pneumoniae* and neutrophil proportion compared to the untreated group. Additionally, the results indicated that nanoparticles encapsulated ampicillin can effectively reduce the number of lung *Streptococcus pneumoniae* and neutrophil proportion. The experimental results demonstrate that ampicillin encapsulated in nanoparticles can exhibit its antibacterial effect.

Example 3: Analysis of Diversity and Composition Changes of Mouse Gut Microbiota Treated with Orally Administered PGNPs-Encapsulated Antibiotics Experimental Method Mice were divided into four groups, each consisting of no less than four mice. The control group was not given any antibiotic treatment, while the experimental group was treated with either free antibiotics or PGNPs-encapsulated antibiotics prepared as described in the above example. Adult mice were orally administered ampicillin and kanamycin (20 mg $kg^{-1}$) or PGNPs-encapsulated ampicillin and kanamycin once a day for five consecutive days. Mouse feces were collected, and total DNA was extracted from fecal samples, and the concentration was measured. The V4 region of 16S rRNA was amplified and sequenced for analysis to determine the effects of two different antibiotic treatments on the diversity and composition of gut microbiota.

```
Forward primer (515FB, SEQ ID NO: 1-97):

AATGATACGGCGACCACCGAGATCTACACGCTXXXXXXXXXXXXTATGG
TAATTGTGTGYCAGCMGCCGCGGTAA
```

where XXXXXXXXXXXXXXX represents the barcode of the primer used for specific labeling of different samples;

```
Reverse primer (806RB, SEQ ID NO: 98):
CAAGCAGAAGACGGCATACGAGATAGTCAGCCAGCCGGACTACNVGGGT
WTCTAAT.
```

The reagents used for amplification are as follows

| Reagent | Volume |
|---|---|
| PCR-grade water | 13.0 μL |
| PCR enzyme (2×) | 10.0 μL |
| Forward primer (10 μM) | 0.5 μL |
| Reverse primer (10 μM) | 0.5 μL |
| Template DNA | 1.0 μL |
| Total volume | 25.0 μL |

The amplification conditions are as follows

| Temperature | Time | Cycle number |
|---|---|---|
| 94° C. | 3 min | |
| 94° C. | 45 s | ×30 |
| 50° C. | 60 s | ×30 |
| 72° C. | 90 s | ×30 |
| 72° C. | 10 min | |
| 4° C. | hold | |

Experimental Results

The changes in α-diversity and β-diversity of the intestinal microbiota in mice are shown in FIG. 5. As shown in FIG. 4, oral administration of nanoparticle-encapsulated ampicillin and vancomycin (PGNPs-Abx) can protect the diversity of the intestinal microbiota, and almost does not affect the structure of the intestinal microbiota, which is beneficial for the recovery of the intestinal microbiota.

Example 4: Oral Administration of PGNPs-Encapsulated Antibiotics Can Protect Against Clinical Complications Caused by Dysbiosis of the Gut Microbiota The gut microbiota plays a crucial regulatory role in host metabolism, especially in the modulation of host energy homeostasis. Some metabolic disorders, such as obesity, are closely associated with gut dysbiosis. Therefore, this example used a mouse model of obesity, an opportunistic pathogen infection model, and detection of the copy number of the beta-lactamase resistance gene ampC in mouse feces to confirm the protective effect of nanoparticle-encapsulated antibiotics on the gut microbiota.

Experimental Method: (Obesity Model)

Mice were divided into four groups, two control groups receiving no oral antibiotics and two experimental groups receiving oral antibiotics. Adult mice were orally administered free ampicillin and vancomycin, as well as PGNPs encapsulated with ampicillin and vancomycin prepared according to the above example (20 mg $kg^{-1}$) once a day for five consecutive days at 5 weeks of age. Control mice were orally administered water and PGNPs without encapsulated antibiotics. At 9 weeks of age, mice were fed a high-fat diet and their weight and fat content were measured to verify the effects of the two different antibiotic treatments on mouse obesity.

Experimental Results

The statistical graphs of mouse weight and fat weight are shown in FIG. 6. The results indicated that mice orally administered with antibiotics encapsulated in PGNPs exhibit the same trend in weight and fat weight as the control mice when fed with high-fat food. However, when mice were treated with free antibiotics and fed high-fat food, their weight and fat weight increased significantly. The experimental results indicate that oral administration of free antibiotics can disrupt the gut microbiota, leading to the occurrence of metabolic diseases such as obesity, while antibiotics encapsulated in PGNPs do not disrupt the gut microbiota of mice.

Experimental Method: (Opportunistic Pathogen Model)

Mice were divided into four groups, with two control groups receiving no oral antibiotics and two experimental groups receiving oral administration of ampicillin and vancomycin, as well as ampicillin and vancomycin coated with PGNPs prepared according to the above-described embodiment (20 mg $kg^{-1}$), once a day for 5 consecutive days. Control mice were administered water orally and PGNPs without antibiotics. On the second day after oral administration, the mice were orally infected with *Citrobacter rodentium*. On the 8 day after infection, the bacterial colony counts of *Citrobacter rodentium* in the feces, cecum, and colon of the mice were analyzed.

Experimental Results

The bacterial colony count statistics of mouse feces, cecum, and colon are shown in FIG. 7. The mice orally administered with antibiotics encapsulated in PGNPs showed a consistent trend in bacterial count with the control mice after infection with *Citrobacter rodentium*. However, the bacterial count significantly increased after treatment with free antibiotics. The experimental results indicate that oral administration of free antibiotics can disrupt the intestinal microbiota, thereby increasing susceptibility to opportunistic pathogen infections, while antibiotics encapsulated in PGNPs do not disrupt the mouse gut microbiota.

Experimental Method: (Resistance Gene Determination)

Mice were divided into four groups, with 6 mice in each group. The control group was not treated with antibiotics, while the experimental group was given free antibiotics or antibiotics encapsulated in PGNPs prepared as described above. The experimental group mice were orally administered ampicillin (20 mg $kg^{-1}$) and PGNPs-encapsulated ampicillin once a day for 5 consecutive days. At specific time points, mouse feces were collected, and total DNA was extracted from fecal samples, and the concentration was measured. Real-time quantitative PCR was used to amplify the ampicillin resistance gene ampC and the total bacterial 16S rRNA in fecal DNA, and the copy numbers of the two genes were calculated to determine the effect of the two different antibiotic treatments on the abundance of antibiotic-resistant bacteria in the gut.

Experimental Results

The changes in copy number of intestinal antibiotic resistance genes in mice are shown in FIG. 8. The results suggested administration of ampicillin nanoparticles wrapped in PEG-PLGA modified with glucose (PGNPs-Amp) and the control group had consistent trends, which could protect the intestinal microbiota and almost did not affect the copy number of ampC antibiotic resistance genes in the intestinal microbiota. However, treatment with free antibiotics in mice disrupted the original balance of the intestinal microbiota, leading to a sharp increase and accumulation of ampC resistance genes. The two different antibiotic treatments did not have a significant impact on the total bacterial copy number.

The above embodiment studied the characteristics of antibiotics wrapped in nanoparticles using glucose-modified PEG-PLGA. The study showed that PEG-PLGA modified with other monosaccharides (such as fructose, trehalose, lactose, and mannose) has similar properties to glucose-modified PEG-PLGA and can be used to prepare antibiotics wrapped in nanoparticles with similar effects.

The specific embodiments described above provide a further detailed explanation of the purpose, technical solutions, and beneficial effects of the present invention. It showed that the above embodiments are merely examples of the present invention and are not intended to limit the scope of the present invention. Any modifications, equivalents, improvements, etc. made within the spirit and principles of the present invention should be included within the scope of the present invention.

What is claimed is:

1. A method comprising orally administering a nanoparticle comprising an antibiotic, a cationic lipid, and a biodegradable and biocompatible polymer encapsulating the antibiotic, wherein the biodegradable and biocompatible polymer comprises a monosaccharide-modified poly (ethylene glycol)-poly (lactic-co-glycolic acid) (PEG-PLGA), wherein the monosaccharide-modified PEG-PLGA is selected from one or more of glucose-PEG-PLGA, fructose-PEG-PLGA, and trehalose-PEG-PLGA, and wherein the antibiotic is absorbed into the bloodstream from the small intestine.

2. The method of claim 1, wherein the weight ratio of the antibiotic to the biodegradable and biocompatible polymer is 1:0.5-5.

3. The method of claim 1, wherein the cationic lipid is selected from one or more of 1,2-dioleoyl-3-trimethylammonium-propane chloride (DOTAP), chloro-2,3-dioleyloxy-propyl)-trimethylammonium (DOTMA), and (3β-[N—(N',N'-dimethylaminoethane)carbamoyl] cholesterol (DC-Chol).

4. The method of claim 1, wherein the weight ratio of the antibiotic to the cationic lipid is 1:0.1-1.

5. The method of claim 1, wherein the antibiotic comprises an active ingredient that affects the intestinal flora.

6. The method of claim 5, wherein the antibiotic is selected from one or more of quinolone antibiotics, β-lactam antibiotics, macrolide antibiotics, aminoglycoside antibiotics, oxazolidinone antibiotics, nitroimidazole antibiotics, tetracycline antibiotics, and glycopeptide antibiotics.

7. The method of claim 3, wherein the weight ratio of the antibiotic to the cationic lipid is 1:0.1-1.

8. The method of claim 2, wherein the weight ratio of the antibiotic to the biodegradable and biocompatible polymer is 1:1, 1:2, 1:3, or 1:4.

9. The method of claim 4, wherein the weight ratio of the antibiotic to the cationic lipid is 1:0.2, 1:0.3, 1:0.5, or 1:0.8.

10. The method of claim 7, wherein the weight ratio of the antibiotic to the cationic lipid is 1:0.2, 1:0.3, 1:0.5, or 1:0.8.

* * * * *

SEQUENCE LISTING

```
<160> NUMBER OF SEQ ID NOS: 98

<210> SEQ ID NO 1
<211> LENGTH: 75
<212> TYPE: DNA
<213> ORGANISM: Artificial Sequence
<220> FEATURE:
<223> OTHER INFORMATION: Synthetic

<400> SEQUENCE: 1

aatgatacgg cgaccaccga gatctacacg ctagccttcg tcgctatggt aattgtgtgy     60

cagcmgccgc ggtaa                                                      75


<210> SEQ ID NO 2
<211> LENGTH: 75
<212> TYPE: DNA
<213> ORGANISM: Artificial Sequence
<220> FEATURE:
<223> OTHER INFORMATION: Synthetic

<400> SEQUENCE: 2

aatgatacgg cgaccaccga gatctacacg cttccatacc ggaatatggt aattgtgtgy     60

cagcmgccgc ggtaa                                                      75


<210> SEQ ID NO 3
<211> LENGTH: 75
<212> TYPE: DNA
<213> ORGANISM: Artificial Sequence
<220> FEATURE:
<223> OTHER INFORMATION: Synthetic

<400> SEQUENCE: 3

aatgatacgg cgaccaccga gatctacacg ctagccctgc tacatatggt aattgtgtgy     60

cagcmgccgc ggtaa                                                      75


<210> SEQ ID NO 4
<211> LENGTH: 75
<212> TYPE: DNA
<213> ORGANISM: Artificial Sequence
<220> FEATURE:
<223> OTHER INFORMATION: Synthetic

<400> SEQUENCE: 4

aatgatacgg cgaccaccga gatctacacg ctcctaacgg tccatatggt aattgtgtgy     60
```

cagcmgccgc ggtaa 75

<210> SEQ ID NO 5
<211> LENGTH: 75
<212> TYPE: DNA
<213> ORGANISM: Artificial Sequence
<220> FEATURE:
<223> OTHER INFORMATION: Synthetic

<400> SEQUENCE: 5
aatgatacgg cgaccaccga gatctacacg ctcgcgcctt aaactatggt aattgtgtgy 60
cagcmgccgc ggtaa 75

<210> SEQ ID NO 6
<211> LENGTH: 75
<212> TYPE: DNA
<213> ORGANISM: Artificial Sequence
<220> FEATURE:
<223> OTHER INFORMATION: Synthetic

<400> SEQUENCE: 6
aatgatacgg cgaccaccga gatctacacg cttatggtac ccagtatggt aattgtgtgy 60
cagcmgccgc ggtaa 75

<210> SEQ ID NO 7
<211> LENGTH: 75
<212> TYPE: DNA
<213> ORGANISM: Artificial Sequence
<220> FEATURE:
<223> OTHER INFORMATION: Synthetic

<400> SEQUENCE: 7
aatgatacgg cgaccaccga gatctacacg cttacaatat ctgttatggt aattgtgtgy 60
cagcmgccgc ggtaa 75

<210> SEQ ID NO 8
<211> LENGTH: 75
<212> TYPE: DNA
<213> ORGANISM: Artificial Sequence
<220> FEATURE:
<223> OTHER INFORMATION: Synthetic

<400> SEQUENCE: 8
aatgatacgg cgaccaccga gatctacacg ctaatttagg taggtatggt aattgtgtgy 60
cagcmgccgc ggtaa 75

<210> SEQ ID NO 9
<211> LENGTH: 75
<212> TYPE: DNA
<213> ORGANISM: Artificial Sequence
<220> FEATURE:
<223> OTHER INFORMATION: Synthetic

<400> SEQUENCE: 9
aatgatacgg cgaccaccga gatctacacg ctgactcaac cagttatggt aattgtgtgy 60
cagcmgccgc ggtaa 75

<210> SEQ ID NO 10
<211> LENGTH: 75
<212> TYPE: DNA
<213> ORGANISM: Artificial Sequence
<220> FEATURE:

<223> OTHER INFORMATION: Synthetic

<400> SEQUENCE: 10
aatgatacgg cgaccaccga gatctacacg ctgcctctac gtcgtatggt aattgtgtgy 60
cagcmgccgc ggtaa 75

<210> SEQ ID NO 11
<211> LENGTH: 75
<212> TYPE: DNA
<213> ORGANISM: Artificial Sequence
<220> FEATURE:
<223> OTHER INFORMATION: Synthetic

<400> SEQUENCE: 11
aatgatacgg cgaccaccga gatctacacg ctactactga ggattatggt aattgtgtgy 60
cagcmgccgc ggtaa 75

<210> SEQ ID NO 12
<211> LENGTH: 75
<212> TYPE: DNA
<213> ORGANISM: Artificial Sequence
<220> FEATURE:
<223> OTHER INFORMATION: Synthetic

<400> SEQUENCE: 12
aatgatacgg cgaccaccga gatctacacg ctaattcacc tccttatggt aattgtgtgy 60
cagcmgccgc ggtaa 75

<210> SEQ ID NO 13
<211> LENGTH: 75
<212> TYPE: DNA
<213> ORGANISM: Artificial Sequence
<220> FEATURE:
<223> OTHER INFORMATION: Synthetic

<400> SEQUENCE: 13
aatgatacgg cgaccaccga gatctacacg ctcgtataaa tgcgtatggt aattgtgtgy 60
cagcmgccgc ggtaa 75

<210> SEQ ID NO 14
<211> LENGTH: 75
<212> TYPE: DNA
<213> ORGANISM: Artificial Sequence
<220> FEATURE:
<223> OTHER INFORMATION: Synthetic

<400> SEQUENCE: 14
aatgatacgg cgaccaccga gatctacacg ctatgctgca acactatggt aattgtgtgy 60
cagcmgccgc ggtaa 75

<210> SEQ ID NO 15
<211> LENGTH: 75
<212> TYPE: DNA
<213> ORGANISM: Artificial Sequence
<220> FEATURE:
<223> OTHER INFORMATION: Synthetic

<400> SEQUENCE: 15
aatgatacgg cgaccaccga gatctacacg ctactcgctc gctgtatggt aattgtgtgy 60
cagcmgccgc ggtaa 75

<210> SEQ ID NO 16
<211> LENGTH: 75
<212> TYPE: DNA
<213> ORGANISM: Artificial Sequence
<220> FEATURE:
<223> OTHER INFORMATION: Synthetic

<400> SEQUENCE: 16
aatgatacgg cgaccaccga gatctacacg ctttccttag tagttatggt aattgtgtgy 60
cagcmgccgc ggtaa 75

<210> SEQ ID NO 17
<211> LENGTH: 75
<212> TYPE: DNA
<213> ORGANISM: Artificial Sequence
<220> FEATURE:
<223> OTHER INFORMATION: Synthetic

<400> SEQUENCE: 17
aatgatacgg cgaccaccga gatctacacg ctcgtccgta tgaatatggt aattgtgtgy 60
cagcmgccgc ggtaa 75

<210> SEQ ID NO 18
<211> LENGTH: 75
<212> TYPE: DNA
<213> ORGANISM: Artificial Sequence
<220> FEATURE:
<223> OTHER INFORMATION: Synthetic

<400> SEQUENCE: 18
aatgatacgg cgaccaccga gatctacacg ctacgtgagg aacgtatggt aattgtgtgy 60
cagcmgccgc ggtaa 75

<210> SEQ ID NO 19
<211> LENGTH: 75
<212> TYPE: DNA
<213> ORGANISM: Artificial Sequence
<220> FEATURE:
<223> OTHER INFORMATION: Synthetic

<400> SEQUENCE: 19
aatgatacgg cgaccaccga gatctacacg ctggttgccc tgtatatggt aattgtgtgy 60
cagcmgccgc ggtaa 75

<210> SEQ ID NO 20
<211> LENGTH: 75
<212> TYPE: DNA
<213> ORGANISM: Artificial Sequence
<220> FEATURE:
<223> OTHER INFORMATION: Synthetic

<400> SEQUENCE: 20
aatgatacgg cgaccaccga gatctacacg ctcatatagc ccgatatggt aattgtgtgy 60
cagcmgccgc ggtaa 75

<210> SEQ ID NO 21
<211> LENGTH: 75
<212> TYPE: DNA
<213> ORGANISM: Artificial Sequence
<220> FEATURE:
<223> OTHER INFORMATION: Synthetic

<400> SEQUENCE: 21
aatgatacgg cgaccaccga gatctacacg ctgcctatga gatctatggt aattgtgtgy 60
cagcmgccgc ggtaa 75

<210> SEQ ID NO 22
<211> LENGTH: 75
<212> TYPE: DNA
<213> ORGANISM: Artificial Sequence
<220> FEATURE:
<223> OTHER INFORMATION: Synthetic

<400> SEQUENCE: 22
aatgatacgg cgaccaccga gatctacacg ctcaagtgaa gggatatggt aattgtgtgy 60
cagcmgccgc ggtaa 75

<210> SEQ ID NO 23
<211> LENGTH: 75
<212> TYPE: DNA
<213> ORGANISM: Artificial Sequence
<220> FEATURE:
<223> OTHER INFORMATION: Synthetic

<400> SEQUENCE: 23
aatgatacgg cgaccaccga gatctacacg ctcacgttta ttcctatggt aattgtgtgy 60
cagcmgccgc ggtaa 75

<210> SEQ ID NO 24
<211> LENGTH: 75
<212> TYPE: DNA
<213> ORGANISM: Artificial Sequence
<220> FEATURE:
<223> OTHER INFORMATION: Synthetic

<400> SEQUENCE: 24
aatgatacgg cgaccaccga gatctacacg cttaatcggt gccatatggt aattgtgtgy 60
cagcmgccgc ggtaa 75

<210> SEQ ID NO 25
<211> LENGTH: 75
<212> TYPE: DNA
<213> ORGANISM: Artificial Sequence
<220> FEATURE:
<223> OTHER INFORMATION: Synthetic

<400> SEQUENCE: 25
aatgatacgg cgaccaccga gatctacacg cttgactaat ggcctatggt aattgtgtgy 60
cagcmgccgc ggtaa 75

<210> SEQ ID NO 26
<211> LENGTH: 75
<212> TYPE: DNA
<213> ORGANISM: Artificial Sequence
<220> FEATURE:
<223> OTHER INFORMATION: Synthetic

<400> SEQUENCE: 26
aatgatacgg cgaccaccga gatctacacg ctcgggacac ccgatatggt aattgtgtgy 60
cagcmgccgc ggtaa 75

<210> SEQ ID NO 27
<211> LENGTH: 75
<212> TYPE: DNA
<213> ORGANISM: Artificial Sequence
<220> FEATURE:
<223> OTHER INFORMATION: Synthetic

<400> SEQUENCE: 27
aatgatacgg cgaccaccga gatctacacg ctctgtctat actatatggt aattgtgtgy 60
cagcmgccgc ggtaa 75

<210> SEQ ID NO 28
<211> LENGTH: 75
<212> TYPE: DNA
<213> ORGANISM: Artificial Sequence
<220> FEATURE:
<223> OTHER INFORMATION: Synthetic

<400> SEQUENCE: 28
aatgatacgg cgaccaccga gatctacacg cttatgccag agattatggt aattgtgtgy 60
cagcmgccgc ggtaa 75

<210> SEQ ID NO 29
<211> LENGTH: 75
<212> TYPE: DNA
<213> ORGANISM: Artificial Sequence
<220> FEATURE:
<223> OTHER INFORMATION: Synthetic

<400> SEQUENCE: 29
aatgatacgg cgaccaccga gatctacacg ctcgtttgga atgatatggt aattgtgtgy 60
cagcmgccgc ggtaa 75

<210> SEQ ID NO 30
<211> LENGTH: 75
<212> TYPE: DNA
<213> ORGANISM: Artificial Sequence
<220> FEATURE:
<223> OTHER INFORMATION: Synthetic

<400> SEQUENCE: 30
aatgatacgg cgaccaccga gatctacacg ctaagaactc atgatatggt aattgtgtgy 60
cagcmgccgc ggtaa 75

<210> SEQ ID NO 31
<211> LENGTH: 75
<212> TYPE: DNA
<213> ORGANISM: Artificial Sequence
<220> FEATURE:
<223> OTHER INFORMATION: Synthetic

<400> SEQUENCE: 31
aatgatacgg cgaccaccga gatctacacg cttgatatcg tctttatggt aattgtgtgy 60
cagcmgccgc ggtaa 75

<210> SEQ ID NO 32
<211> LENGTH: 75
<212> TYPE: DNA
<213> ORGANISM: Artificial Sequence
<220> FEATURE:
<223> OTHER INFORMATION: Synthetic

<400> SEQUENCE: 32
aatgatacgg cgaccaccga gatctacacg ctcggtgacc tacttatggt aattgtgtgy 60
cagcmgccgc ggtaa 75

<210> SEQ ID NO 33
<211> LENGTH: 75
<212> TYPE: DNA
<213> ORGANISM: Artificial Sequence
<220> FEATURE:
<223> OTHER INFORMATION: Synthetic

<400> SEQUENCE: 33
aatgatacgg cgaccaccga gatctacacg ctaatgcgcg tatatatggt aattgtgtgy 60
cagcmgccgc ggtaa 75

<210> SEQ ID NO 34
<211> LENGTH: 75
<212> TYPE: DNA
<213> ORGANISM: Artificial Sequence
<220> FEATURE:
<223> OTHER INFORMATION: Synthetic

<400> SEQUENCE: 34
aatgatacgg cgaccaccga gatctacacg ctcttgattc ttgatatggt aattgtgtgy 60
cagcmgccgc ggtaa 75

<210> SEQ ID NO 35
<211> LENGTH: 75
<212> TYPE: DNA
<213> ORGANISM: Artificial Sequence
<220> FEATURE:
<223> OTHER INFORMATION: Synthetic

<400> SEQUENCE: 35
aatgatacgg cgaccaccga gatctacacg ctgaaatctt gaagtatggt aattgtgtgy 60
cagcmgccgc ggtaa 75

<210> SEQ ID NO 36
<211> LENGTH: 75
<212> TYPE: DNA
<213> ORGANISM: Artificial Sequence
<220> FEATURE:
<223> OTHER INFORMATION: Synthetic

<400> SEQUENCE: 36
aatgatacgg cgaccaccga gatctacacg ctgagataca gttctatggt aattgtgtgy 60
cagcmgccgc ggtaa 75

<210> SEQ ID NO 37
<211> LENGTH: 75
<212> TYPE: DNA
<213> ORGANISM: Artificial Sequence
<220> FEATURE:
<223> OTHER INFORMATION: Synthetic

<400> SEQUENCE: 37
aatgatacgg cgaccaccga gatctacacg ctgtggagtc tcattatggt aattgtgtgy 60
cagcmgccgc ggtaa 75

<210> SEQ ID NO 38
<211> LENGTH: 75
<212> TYPE: DNA
<213> ORGANISM: Artificial Sequence
<220> FEATURE:
<223> OTHER INFORMATION: Synthetic

<400> SEQUENCE: 38
aatgatacgg cgaccaccga gatctacacg ctaccttaca cctttatggt aattgtgtgy 60
cagcmgccgc ggtaa 75

<210> SEQ ID NO 39
<211> LENGTH: 75
<212> TYPE: DNA
<213> ORGANISM: Artificial Sequence
<220> FEATURE:
<223> OTHER INFORMATION: Synthetic

<400> SEQUENCE: 39
aatgatacgg cgaccaccga gatctacacg cttaatctcg ccggtatggt aattgtgtgy 60
cagcmgccgc ggtaa 75

<210> SEQ ID NO 40
<211> LENGTH: 75
<212> TYPE: DNA
<213> ORGANISM: Artificial Sequence
<220> FEATURE:
<223> OTHER INFORMATION: Synthetic

<400> SEQUENCE: 40
aatgatacgg cgaccaccga gatctacacg ctatctagtg gcaatatggt aattgtgtgy 60
cagcmgccgc ggtaa 75

<210> SEQ ID NO 41
<211> LENGTH: 75
<212> TYPE: DNA
<213> ORGANISM: Artificial Sequence
<220> FEATURE:
<223> OTHER INFORMATION: Synthetic

<400> SEQUENCE: 41
aatgatacgg cgaccaccga gatctacacg ctacgcttaa cgactatggt aattgtgtgy 60
cagcmgccgc ggtaa 75

<210> SEQ ID NO 42
<211> LENGTH: 75
<212> TYPE: DNA
<213> ORGANISM: Artificial Sequence
<220> FEATURE:
<223> OTHER INFORMATION: Synthetic

<400> SEQUENCE: 42
aatgatacgg cgaccaccga gatctacacg cttacggatt atggtatggt aattgtgtgy 60
cagcmgccgc ggtaa 75

<210> SEQ ID NO 43
<211> LENGTH: 75
<212> TYPE: DNA
<213> ORGANISM: Artificial Sequence
<220> FEATURE:
<223> OTHER INFORMATION: Synthetic

<400> SEQUENCE: 43
aatgatacgg cgaccaccga gatctacacg ctatacatgc aagatatggt aattgtgtgy 60
cagcmgccgc ggtaa 75

<210> SEQ ID NO 44
<211> LENGTH: 75
<212> TYPE: DNA

<213> ORGANISM: Artificial Sequence
<220> FEATURE:
<223> OTHER INFORMATION: Synthetic

<400> SEQUENCE: 44
aatgatacgg cgaccaccga gatctacacg ctcttagtgc agaatatggt aattgtgtgy 60
cagcmgccgc ggtaa 75

<210> SEQ ID NO 45
<211> LENGTH: 75
<212> TYPE: DNA
<213> ORGANISM: Artificial Sequence
<220> FEATURE:
<223> OTHER INFORMATION: Synthetic

<400> SEQUENCE: 45
aatgatacgg cgaccaccga gatctacacg ctaatcttgc gccgtatggt aattgtgtgy 60
cagcmgccgc ggtaa 75

<210> SEQ ID NO 46
<211> LENGTH: 75
<212> TYPE: DNA
<213> ORGANISM: Artificial Sequence
<220> FEATURE:
<223> OTHER INFORMATION: Synthetic

<400> SEQUENCE: 46
aatgatacgg cgaccaccga gatctacacg ctaggatcag ggaatatggt aattgtgtgy 60
cagcmgccgc ggtaa 75

<210> SEQ ID NO 47
<211> LENGTH: 75
<212> TYPE: DNA
<213> ORGANISM: Artificial Sequence
<220> FEATURE:
<223> OTHER INFORMATION: Synthetic

<400> SEQUENCE: 47
aatgatacgg cgaccaccga gatctacacg ctaataacta gggttatggt aattgtgtgy 60
cagcmgccgc ggtaa 75

<210> SEQ ID NO 48
<211> LENGTH: 75
<212> TYPE: DNA
<213> ORGANISM: Artificial Sequence
<220> FEATURE:
<223> OTHER INFORMATION: Synthetic

<400> SEQUENCE: 48
aatgatacgg cgaccaccga gatctacacg cttattgcag cagctatggt aattgtgtgy 60
cagcmgccgc ggtaa 75

<210> SEQ ID NO 49
<211> LENGTH: 75
<212> TYPE: DNA
<213> ORGANISM: Artificial Sequence
<220> FEATURE:
<223> OTHER INFORMATION: Synthetic

<400> SEQUENCE: 49
aatgatacgg cgaccaccga gatctacacg cttgatgtgc taagtatggt aattgtgtgy 60
cagcmgccgc ggtaa 75

<210> SEQ ID NO 50
<211> LENGTH: 75
<212> TYPE: DNA
<213> ORGANISM: Artificial Sequence
<220> FEATURE:
<223> OTHER INFORMATION: Synthetic

<400> SEQUENCE: 50
aatgatacgg cgaccaccga gatctacacg ctgtagtaga ccattatggt aattgtgtgy 60
cagcmgccgc ggtaa 75

<210> SEQ ID NO 51
<211> LENGTH: 75
<212> TYPE: DNA
<213> ORGANISM: Artificial Sequence
<220> FEATURE:
<223> OTHER INFORMATION: Synthetic

<400> SEQUENCE: 51
aatgatacgg cgaccaccga gatctacacg ctagtaaaga tcgttatggt aattgtgtgy 60
cagcmgccgc ggtaa 75

<210> SEQ ID NO 52
<211> LENGTH: 75
<212> TYPE: DNA
<213> ORGANISM: Artificial Sequence
<220> FEATURE:
<223> OTHER INFORMATION: Synthetic

<400> SEQUENCE: 52
aatgatacgg cgaccaccga gatctacacg ctctcgccct cgcctatggt aattgtgtgy 60
cagcmgccgc ggtaa 75

<210> SEQ ID NO 53
<211> LENGTH: 75
<212> TYPE: DNA
<213> ORGANISM: Artificial Sequence
<220> FEATURE:
<223> OTHER INFORMATION: Synthetic

<400> SEQUENCE: 53
aatgatacgg cgaccaccga gatctacacg cttctctttc gacatatggt aattgtgtgy 60
cagcmgccgc ggtaa 75

<210> SEQ ID NO 54
<211> LENGTH: 75
<212> TYPE: DNA
<213> ORGANISM: Artificial Sequence
<220> FEATURE:
<223> OTHER INFORMATION: Synthetic

<400> SEQUENCE: 54
aatgatacgg cgaccaccga gatctacacg ctacatactg agcatatggt aattgtgtgy 60
cagcmgccgc ggtaa 75

<210> SEQ ID NO 55
<211> LENGTH: 75
<212> TYPE: DNA
<213> ORGANISM: Artificial Sequence
<220> FEATURE:
<223> OTHER INFORMATION: Synthetic

<400> SEQUENCE: 55
aatgatacgg cgaccaccga gatctacacg ctgttgatac gatgtatggt aattgtgtgy 60
cagcmgccgc ggtaa 75

<210> SEQ ID NO 56
<211> LENGTH: 75
<212> TYPE: DNA
<213> ORGANISM: Artificial Sequence
<220> FEATURE:
<223> OTHER INFORMATION: Synthetic

<400> SEQUENCE: 56
aatgatacgg cgaccaccga gatctacacg ctgtcaacgc tgtctatggt aattgtgtgy 60
cagcmgccgc ggtaa 75

<210> SEQ ID NO 57
<211> LENGTH: 75
<212> TYPE: DNA
<213> ORGANISM: Artificial Sequence
<220> FEATURE:
<223> OTHER INFORMATION: Synthetic

<400> SEQUENCE: 57
aatgatacgg cgaccaccga gatctacacg cttgagaccc tacatatggt aattgtgtgy 60
cagcmgccgc ggtaa 75

<210> SEQ ID NO 58
<211> LENGTH: 75
<212> TYPE: DNA
<213> ORGANISM: Artificial Sequence
<220> FEATURE:
<223> OTHER INFORMATION: Synthetic

<400> SEQUENCE: 58
aatgatacgg cgaccaccga gatctacacg ctacttggtg taagtatggt aattgtgtgy 60
cagcmgccgc ggtaa 75

<210> SEQ ID NO 59
<211> LENGTH: 75
<212> TYPE: DNA
<213> ORGANISM: Artificial Sequence
<220> FEATURE:
<223> OTHER INFORMATION: Synthetic

<400> SEQUENCE: 59
aatgatacgg cgaccaccga gatctacacg ctattacgta tcattatggt aattgtgtgy 60
cagcmgccgc ggtaa 75

<210> SEQ ID NO 60
<211> LENGTH: 75
<212> TYPE: DNA
<213> ORGANISM: Artificial Sequence
<220> FEATURE:
<223> OTHER INFORMATION: Synthetic

<400> SEQUENCE: 60
aatgatacgg cgaccaccga gatctacacg ctcacgcagt ctactatggt aattgtgtgy 60
cagcmgccgc ggtaa 75

<210> SEQ ID NO 61
<211> LENGTH: 75

<212> TYPE: DNA
<213> ORGANISM: Artificial Sequence
<220> FEATURE:
<223> OTHER INFORMATION: Synthetic

<400> SEQUENCE: 61
aatgatacgg cgaccaccga gatctacacg cttgtgcacg ccattatggt aattgtgtgy 60
cagcmgccgc ggtaa 75

<210> SEQ ID NO 62
<211> LENGTH: 75
<212> TYPE: DNA
<213> ORGANISM: Artificial Sequence
<220> FEATURE:
<223> OTHER INFORMATION: Synthetic

<400> SEQUENCE: 62
aatgatacgg cgaccaccga gatctacacg ctccggacaa gaagtatggt aattgtgtgy 60
cagcmgccgc ggtaa 75

<210> SEQ ID NO 63
<211> LENGTH: 75
<212> TYPE: DNA
<213> ORGANISM: Artificial Sequence
<220> FEATURE:
<223> OTHER INFORMATION: Synthetic

<400> SEQUENCE: 63
aatgatacgg cgaccaccga gatctacacg ctttgctgga cgcttatggt aattgtgtgy 60
cagcmgccgc ggtaa 75

<210> SEQ ID NO 64
<211> LENGTH: 75
<212> TYPE: DNA
<213> ORGANISM: Artificial Sequence
<220> FEATURE:
<223> OTHER INFORMATION: Synthetic

<400> SEQUENCE: 64
aatgatacgg cgaccaccga gatctacacg cttactaacg cggttatggt aattgtgtgy 60
cagcmgccgc ggtaa 75

<210> SEQ ID NO 65
<211> LENGTH: 75
<212> TYPE: DNA
<213> ORGANISM: Artificial Sequence
<220> FEATURE:
<223> OTHER INFORMATION: Synthetic

<400> SEQUENCE: 65
aatgatacgg cgaccaccga gatctacacg ctgcgatcac accttatggt aattgtgtgy 60
cagcmgccgc ggtaa 75

<210> SEQ ID NO 66
<211> LENGTH: 75
<212> TYPE: DNA
<213> ORGANISM: Artificial Sequence
<220> FEATURE:
<223> OTHER INFORMATION: Synthetic

<400> SEQUENCE: 66
aatgatacgg cgaccaccga gatctacacg ctcaaacgca ctaatatggt aattgtgtgy 60
cagcmgccgc ggtaa 75

<210> SEQ ID NO 67
<211> LENGTH: 75
<212> TYPE: DNA
<213> ORGANISM: Artificial Sequence
<220> FEATURE:
<223> OTHER INFORMATION: Synthetic

<400> SEQUENCE: 67
aatgatacgg cgaccaccga gatctacacg ctgaagaggg ttgatatggt aattgtgtgy 60
cagcmgccgc ggtaa 75

<210> SEQ ID NO 68
<211> LENGTH: 75
<212> TYPE: DNA
<213> ORGANISM: Artificial Sequence
<220> FEATURE:
<223> OTHER INFORMATION: Synthetic

<400> SEQUENCE: 68
aatgatacgg cgaccaccga gatctacacg cttgagtggt ctgttatggt aattgtgtgy 60
cagcmgccgc ggtaa 75

<210> SEQ ID NO 69
<211> LENGTH: 75
<212> TYPE: DNA
<213> ORGANISM: Artificial Sequence
<220> FEATURE:
<223> OTHER INFORMATION: Synthetic

<400> SEQUENCE: 69
aatgatacgg cgaccaccga gatctacacg ctttacacaa aggctatggt aattgtgtgy 60
cagcmgccgc ggtaa 75

<210> SEQ ID NO 70
<211> LENGTH: 75
<212> TYPE: DNA
<213> ORGANISM: Artificial Sequence
<220> FEATURE:
<223> OTHER INFORMATION: Synthetic

<400> SEQUENCE: 70
aatgatacgg cgaccaccga gatctacacg ctacgacgca tttgtatggt aattgtgtgy 60
cagcmgccgc ggtaa 75

<210> SEQ ID NO 71
<211> LENGTH: 75
<212> TYPE: DNA
<213> ORGANISM: Artificial Sequence
<220> FEATURE:
<223> OTHER INFORMATION: Synthetic

<400> SEQUENCE: 71
aatgatacgg cgaccaccga gatctacacg cttatccaag cgcatatggt aattgtgtgy 60
cagcmgccgc ggtaa 75

<210> SEQ ID NO 72
<211> LENGTH: 75
<212> TYPE: DNA
<213> ORGANISM: Artificial Sequence
<220> FEATURE:
<223> OTHER INFORMATION: Synthetic

<400> SEQUENCE: 72
aatgatacgg cgaccaccga gatctacacg ctagagccaa gagctatggt aattgtgtgy 60
cagcmgccgc ggtaa 75

<210> SEQ ID NO 73
<211> LENGTH: 75
<212> TYPE: DNA
<213> ORGANISM: Artificial Sequence
<220> FEATURE:
<223> OTHER INFORMATION: Synthetic

<400> SEQUENCE: 73
aatgatacgg cgaccaccga gatctacacg ctggtgagca agcatatggt aattgtgtgy 60
cagcmgccgc ggtaa 75

<210> SEQ ID NO 74
<211> LENGTH: 75
<212> TYPE: DNA
<213> ORGANISM: Artificial Sequence
<220> FEATURE:
<223> OTHER INFORMATION: Synthetic

<400> SEQUENCE: 74
aatgatacgg cgaccaccga gatctacacg cttaaatata cccttatggt aattgtgtgy 60
cagcmgccgc ggtaa 75

<210> SEQ ID NO 75
<211> LENGTH: 75
<212> TYPE: DNA
<213> ORGANISM: Artificial Sequence
<220> FEATURE:
<223> OTHER INFORMATION: Synthetic

<400> SEQUENCE: 75
aatgatacgg cgaccaccga gatctacacg ctttgcggac cctatatggt aattgtgtgy 60
cagcmgccgc ggtaa 75

<210> SEQ ID NO 76
<211> LENGTH: 75
<212> TYPE: DNA
<213> ORGANISM: Artificial Sequence
<220> FEATURE:
<223> OTHER INFORMATION: Synthetic

<400> SEQUENCE: 76
aatgatacgg cgaccaccga gatctacacg ctgtcgtcca aatgtatggt aattgtgtgy 60
cagcmgccgc ggtaa 75

<210> SEQ ID NO 77
<211> LENGTH: 75
<212> TYPE: DNA
<213> ORGANISM: Artificial Sequence
<220> FEATURE:
<223> OTHER INFORMATION: Synthetic

<400> SEQUENCE: 77
aatgatacgg cgaccaccga gatctacacg cttgcacagt cgcttatggt aattgtgtgy 60
cagcmgccgc ggtaa 75

<210> SEQ ID NO 78

<211> LENGTH: 75
<212> TYPE: DNA
<213> ORGANISM: Artificial Sequence
<220> FEATURE:
<223> OTHER INFORMATION: Synthetic

<400> SEQUENCE: 78
aatgatacgg cgaccaccga gatctacacg ctttactgtg gccgtatggt aattgtgtgy 60
cagcmgccgc ggtaa 75

<210> SEQ ID NO 79
<211> LENGTH: 75
<212> TYPE: DNA
<213> ORGANISM: Artificial Sequence
<220> FEATURE:
<223> OTHER INFORMATION: Synthetic

<400> SEQUENCE: 79
aatgatacgg cgaccaccga gatctacacg ctggttcatg aacatatggt aattgtgtgy 60
cagcmgccgc ggtaa 75

<210> SEQ ID NO 80
<211> LENGTH: 75
<212> TYPE: DNA
<213> ORGANISM: Artificial Sequence
<220> FEATURE:
<223> OTHER INFORMATION: Synthetic

<400> SEQUENCE: 80
aatgatacgg cgaccaccga gatctacacg cttaacaata attctatggt aattgtgtgy 60
cagcmgccgc ggtaa 75

<210> SEQ ID NO 81
<211> LENGTH: 75
<212> TYPE: DNA
<213> ORGANISM: Artificial Sequence
<220> FEATURE:
<223> OTHER INFORMATION: Synthetic

<400> SEQUENCE: 81
aatgatacgg cgaccaccga gatctacacg ctcttattaa acgttatggt aattgtgtgy 60
cagcmgccgc ggtaa 75

<210> SEQ ID NO 82
<211> LENGTH: 75
<212> TYPE: DNA
<213> ORGANISM: Artificial Sequence
<220> FEATURE:
<223> OTHER INFORMATION: Synthetic

<400> SEQUENCE: 82
aatgatacgg cgaccaccga gatctacacg ctgctcgaag attctatggt aattgtgtgy 60
cagcmgccgc ggtaa 75

<210> SEQ ID NO 83
<211> LENGTH: 75
<212> TYPE: DNA
<213> ORGANISM: Artificial Sequence
<220> FEATURE:
<223> OTHER INFORMATION: Synthetic

<400> SEQUENCE: 83
aatgatacgg cgaccaccga gatctacacg cttatttgat tggttatggt aattgtgtgy 60
cagcmgccgc ggtaa 75

<210> SEQ ID NO 84
<211> LENGTH: 75
<212> TYPE: DNA
<213> ORGANISM: Artificial Sequence
<220> FEATURE:
<223> OTHER INFORMATION: Synthetic

<400> SEQUENCE: 84
aatgatacgg cgaccaccga gatctacacg cttgtcaaag tgactatggt aattgtgtgy 60
cagcmgccgc ggtaa 75

<210> SEQ ID NO 85
<211> LENGTH: 75
<212> TYPE: DNA
<213> ORGANISM: Artificial Sequence
<220> FEATURE:
<223> OTHER INFORMATION: Synthetic

<400> SEQUENCE: 85
aatgatacgg cgaccaccga gatctacacg ctctatgtat tagttatggt aattgtgtgy 60
cagcmgccgc ggtaa 75

<210> SEQ ID NO 86
<211> LENGTH: 75
<212> TYPE: DNA
<213> ORGANISM: Artificial Sequence
<220> FEATURE:
<223> OTHER INFORMATION: Synthetic

<400> SEQUENCE: 86
aatgatacgg cgaccaccga gatctacacg ctactcccgt gtgatatggt aattgtgtgy 60
cagcmgccgc ggtaa 75

<210> SEQ ID NO 87
<211> LENGTH: 75
<212> TYPE: DNA
<213> ORGANISM: Artificial Sequence
<220> FEATURE:
<223> OTHER INFORMATION: Synthetic

<400> SEQUENCE: 87
aatgatacgg cgaccaccga gatctacacg ctcggtatag caattatggt aattgtgtgy 60
cagcmgccgc ggtaa 75

<210> SEQ ID NO 88
<211> LENGTH: 75
<212> TYPE: DNA
<213> ORGANISM: Artificial Sequence
<220> FEATURE:
<223> OTHER INFORMATION: Synthetic

<400> SEQUENCE: 88
aatgatacgg cgaccaccga gatctacacg ctgactctgc tcagtatggt aattgtgtgy 60
cagcmgccgc ggtaa 75

<210> SEQ ID NO 89
<211> LENGTH: 75
<212> TYPE: DNA
<213> ORGANISM: Artificial Sequence
<220> FEATURE:

<223> OTHER INFORMATION: Synthetic

<400> SEQUENCE: 89
aatgatacgg cgaccaccga gatctacacg ctgtcatgct ccagtatggt aattgtgtgy 60
cagcmgccgc ggtaa 75

<210> SEQ ID NO 90
<211> LENGTH: 75
<212> TYPE: DNA
<213> ORGANISM: Artificial Sequence
<220> FEATURE:
<223> OTHER INFORMATION: Synthetic

<400> SEQUENCE: 90
aatgatacgg cgaccaccga gatctacacg cttaccgaag gtattatggt aattgtgtgy 60
cagcmgccgc ggtaa 75

<210> SEQ ID NO 91
<211> LENGTH: 75
<212> TYPE: DNA
<213> ORGANISM: Artificial Sequence
<220> FEATURE:
<223> OTHER INFORMATION: Synthetic

<400> SEQUENCE: 91
aatgatacgg cgaccaccga gatctacacg cttgagtatg agtatatggt aattgtgtgy 60
cagcmgccgc ggtaa 75

<210> SEQ ID NO 92
<211> LENGTH: 75
<212> TYPE: DNA
<213> ORGANISM: Artificial Sequence
<220> FEATURE:
<223> OTHER INFORMATION: Synthetic

<400> SEQUENCE: 92
aatgatacgg cgaccaccga gatctacacg ctaatggttc agcatatggt aattgtgtgy 60
cagcmgccgc ggtaa 75

<210> SEQ ID NO 93
<211> LENGTH: 75
<212> TYPE: DNA
<213> ORGANISM: Artificial Sequence
<220> FEATURE:
<223> OTHER INFORMATION: Synthetic

<400> SEQUENCE: 93
aatgatacgg cgaccaccga gatctacacg ctgaaccagt actctatggt aattgtgtgy 60
cagcmgccgc ggtaa 75

<210> SEQ ID NO 94
<211> LENGTH: 75
<212> TYPE: DNA
<213> ORGANISM: Artificial Sequence
<220> FEATURE:
<223> OTHER INFORMATION: Synthetic

<400> SEQUENCE: 94
aatgatacgg cgaccaccga gatctacacg ctcgcaccca tacatatggt aattgtgtgy 60
cagcmgccgc ggtaa 75

-continued

<210> SEQ ID NO 95
<211> LENGTH: 75
<212> TYPE: DNA
<213> ORGANISM: Artificial Sequence
<220> FEATURE:
<223> OTHER INFORMATION: Synthetic

<400> SEQUENCE: 95
aatgatacgg cgaccaccga gatctacacg ctgtgccata atcgtatggt aattgtgtgy 60
cagcmgccgc ggtaa 75

<210> SEQ ID NO 96
<211> LENGTH: 75
<212> TYPE: DNA
<213> ORGANISM: Artificial Sequence
<220> FEATURE:
<223> OTHER INFORMATION: Synthetic

<400> SEQUENCE: 96
aatgatacgg cgaccaccga gatctacacg ctactcttac ttagtatggt aattgtgtgy 60
cagcmgccgc ggtaa 75

<210> SEQ ID NO 97
<211> LENGTH: 75
<212> TYPE: DNA
<213> ORGANISM: Artificial Sequence
<220> FEATURE:
<223> OTHER INFORMATION: Synthetic

<400> SEQUENCE: 97
aatgatacgg cgaccaccga gatctacacg ctctacaggg tctctatggt aattgtgtgy 60
cagcmgccgc ggtaa 75

<210> SEQ ID NO 98
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (44)..(44)
<223> OTHER INFORMATION: n is a, c, g, or t

<400> SEQUENCE: 98
caagcagaag acggcatacg agatagtcag ccagccggac tacnvgggtw tctaat 56